United States Patent
Pech et al.

(10) Patent No.: US 7,559,919 B2
(45) Date of Patent: Jul. 14, 2009

(54) NEEDLE SHIELD

(75) Inventors: Bernhard Pech, Aachen (DE); Bernd Becker, Aachen (DE); Dirk Zölcher, Kreuzau (DE); Hubert Jansen, Stolberg (DE)

(73) Assignee: West Pharmaceutical Services, Inc., Lionville, PA (US)

( * ) Notice: Subject to any disclaimer, the term of this patent is extended or adjusted under 35 U.S.C. 154(b) by 179 days.

(21) Appl. No.: 11/738,670

(22) Filed: Apr. 23, 2007

(65) Prior Publication Data

US 2007/0250016 A1   Oct. 25, 2007

Related U.S. Application Data

(60) Provisional application No. 60/745,301, filed on Apr. 21, 2006.

(51) Int. Cl.
*A61M 5/32* (2006.01)
(52) U.S. Cl. .................................... 604/192
(58) Field of Classification Search ........... 604/192, 604/263, 187, 198, 110, 111, 197, 199
See application file for complete search history.

(56) References Cited

U.S. PATENT DOCUMENTS

| | | | |
|---|---|---|---|
| 3,434,473 A | | 3/1969 | Smith |
| 3,865,236 A | * | 2/1975 | Rycroft ................... 206/364 |
| 4,240,425 A | * | 12/1980 | Akhavi ..................... 604/199 |
| 4,248,246 A | | 2/1981 | Ikeda |
| 4,300,678 A | | 11/1981 | Gyure et al. |
| 4,430,082 A | | 2/1984 | Schwabacher |
| 4,636,201 A | | 1/1987 | Ambrose et al. |
| 4,735,311 A | | 4/1988 | Lowe |
| 4,747,837 A | | 5/1988 | Hauck |
| 4,964,866 A | | 10/1990 | Szwarc |
| 4,986,818 A | * | 1/1991 | Imbert et al. ............... 604/192 |

(Continued)

FOREIGN PATENT DOCUMENTS

EP  0876824 A2  11/1998

(Continued)

OTHER PUBLICATIONS

Several photographs of Stelmi Trading International needle protecting device, admitted prior art.

*Primary Examiner*—Manuel A Mendez
(74) *Attorney, Agent, or Firm*—Panitch Schwarze Belisario & Nadel LLP

(57) ABSTRACT

A needle shield is removably mountable to a syringe to protect a user from inadvertent needle pricks and limit contamination of a needle of the syringe. The needle shield includes a plug having an external surface and a shell having an inner surface defining a cavity therein. The plug is positioned within the cavity and a portion of the external surface of the plug is in contact with the inner surface of the shell at a contact area. The plug is non-removably bonded to the shell in the contact area by melting a portion of the shell and the plug in the contact area through application of radiation energy. A securing ring may alternatively be fixed to the shell through the application of radiation energy to secure a shoulder of the plug between the ring and a rib of the shell. The radiation energy is preferably applied by laser welding.

17 Claims, 5 Drawing Sheets

U.S. PATENT DOCUMENTS

| | | |
|---|---|---|
| 5,085,647 A | 2/1992 | Henderson et al. |
| 5,098,400 A | 3/1992 | Crouse et al. |
| 5,147,325 A | 9/1992 | Mitchell et al. |
| 5,232,455 A | 8/1993 | Hollister |
| 5,322,515 A | 6/1994 | Karas et al. |
| 5,336,197 A | 8/1994 | Kuracina et al. |
| 5,342,320 A | 8/1994 | Cameron |
| 5,832,971 A | 11/1998 | Yale et al. |
| 5,980,493 A | 11/1999 | Smith et al. |
| 5,980,495 A | 11/1999 | Heniz et al. |
| 5,989,229 A | 11/1999 | Chiappetta |
| 6,183,440 B1 | 2/2001 | Bell |
| 6,186,980 B1 | 2/2001 | Brunel |
| 6,193,696 B1 | 2/2001 | Jansen et al. |
| D460,178 S | 7/2002 | Courteix |
| D461,557 S | 8/2002 | Courteix |
| 6,485,474 B1 | 11/2002 | Heinz et al. |
| D469,178 S | 1/2003 | Courteix |
| 6,551,286 B1 | 4/2003 | Claessens |
| 6,595,954 B1 | 7/2003 | Luther et al. |
| 6,629,963 B2 | 10/2003 | Prais et al. |
| 6,719,732 B2 | 4/2004 | Courteix |
| 7,036,288 B2 | 5/2006 | Vetter et al. |
| 7,094,223 B2 | 8/2006 | Brunel |
| 2002/0062108 A1 | 5/2002 | Courteix |
| 2003/0181859 A1 | 9/2003 | Brunel |
| 2003/0208165 A1 | 11/2003 | Christensen |
| 2004/0186440 A1 | 9/2004 | Jensen et al. |
| 2005/0038391 A1 | 2/2005 | Wittland et al. |
| 2005/0096596 A1 | 5/2005 | Crawford et al. |
| 2006/0184114 A1 | 8/2006 | Tai |

FOREIGN PATENT DOCUMENTS

| | | |
|---|---|---|
| EP | 1099450 B1 | 5/2001 |
| EP | 1208861 B1 | 5/2002 |
| EP | 1502616 A1 | 2/2005 |
| FR | 7045698 | 7/1972 |
| FR | 2777787 | 10/1999 |

* cited by examiner

NEEDLE SHIELD

CROSS-REFERENCE TO RELATED APPLICATIONS

This application claims the benefit of U.S. Provisional Patent Application No. 60/745,301 filed Apr. 21, 2006 the subject matter of which is incorporated herein by reference in its entirety.

BACKGROUND OF THE INVENTION

Needle shields for syringes are well known and typically include a rigid plastic shell or cover with a soft plug or sheath therein. The plug and rigid plastic shell are either separately constructed and assembled by positioning the plug in the shell to form a needle shield or the plastic shell is constructed and the plug is injection molded into the shell to form the needle shield. The needle shield is removably mounted to the needle end of a syringe to protect a user from pricks or sticks from the needle and to avoid exposure of the needle to contaminants. U.S. Pat. No. 4,986,818 discloses a typical needle shield that is removably mountable to a syringe to cover the needle tip and generally protect the needle tip from contamination because the tip is located in the plug in a storage configuration. The needle tip and needle are also stabilized by the plug in the storage configuration to generally prevent damage to the needle and tip and to limit user exposure to the needle tip.

Conventional needle shields constructed utilizing an assembly of a preformed plug positioned in a rigid plastic shell often result in disassembly of the plug and shell when removing the syringe and syringe needle from the needle shield assembly. The plug and shell may become disconnected from one another during removal of the needle from the plug because disassembly forces of the needle shield from the syringe may be quite high over the shelf life of the assembly. In addition, the plug and/or shell may break during disassembly of the syringe and syringe needle from the assembly. For example, the rigid, plastic needle shell or plug may stick to a glass syringe or to the needle making it difficult for a user to remove the needle shield from the syringe, resulting in elevated removal forces. The stickiness or adhesion of the needle shield to the syringe or needle becomes more prominent over time. Accordingly, the plug and shell assembly may become disassembled or the relatively small and thin rigid shell may break or damage the syringe or the syringe needle during disassembly. In addition, various methods for mechanically mounting the pre-formed plug in the rigid plastic shell, for example, crimping, often result in particulates being formed due to the crimping process. In general, particulates are undesirable when assembling a needle shield, as the particulates may contaminate the relatively clean needle shield.

Alternative methods and assemblies for more securely mounting the pre-formed plug in the pre-formed shell complicate the construction of the needle shield. Needle shields that include the plug molded directly into the rigid shell result in an assembly with no air gap between the relatively soft plug and the hard, plastic shell. In situations where the needle of the syringe extends through the soft plug and impacts the hard, plastic shell, the needle tip may become damaged and/or contaminated. If needles that contact the hard, plastic shell are damaged and not detected prior to shipment to a user, the injection using the damaged needle tip may be quite painful for a patient.

During assembly of the needle shield with the syringe, each needle shield and syringe assembly is subjected to testing to determine if the needle tip has extended through the plug and has potentially impacted the hard, plastic shell or is otherwise damaged. The syringe and needle shield assemblies are commonly tested by passing each assembly through an electronic field which results in a spark from an electrical anode to the needle tip when the needle tip has extended through the soft plug. U.S. Pat. No. 6,229,314 B1 ('314 patent) discloses such an electronic field quality assurance test mechanism and method and is incorporated herein by reference. Needle shields that are co-injected into their shells are not adapted for such a test because no air gap is created between the plug and shell wherein a spark may be created at the needle tip.

However, the co-injected needle shields are extremely difficult to disassemble or break by removing the plug from the shell, which may sometimes happen in the mechanically assembled needle shields. Because the plug and shell are connected along an internal surface of the shell, no mechanical devices, clamps or fasteners are needed to secure the plug to the shell. Accordingly, the co-injected needle shield typically eliminates the risk of the plug becoming disassembled or falling out of the shell when the needle shield is removed from the shell. Therefore, the co-injected needle shield has the advantage of being rigidly secured to the shell and the disadvantage of being inappropriate for the electronic field quality assurance test. The mechanically assembled needle shield provides the advantage of being suitable for electronic field quality assurance testing because of the air gap between the plug and shell and the disadvantage of being dislodged from the shell during disassembly of the syringe from the needle shield or a complicated assembly process to more securely mount the plug to the shell.

In addition, the conventional co-injected needle shield restricts flexing of the plug, because the plug is rigidly held within the walls of the shell and is generally unable to flex radially outwardly due to being enclosed by the rigid shell. The restriction of the flexing of the plug in the co-injected needle shields typically increases the insertion and removal forces required to insert the needle tip into the plug and to remove the needle tip from the plug.

It would be desirable to construct a needle shield that includes an air gap between the soft plug and the hard shell, as is present in the mechanically assembled needle shield, such that the electrical field test is able to detect needles that extend completely through the plug while maintaining the advantage of rigid mounting of the plug to the shell in the co-injected needle shield to generally prevent the plug from becoming disengaged from the shell. It would also be desirable for the needle shield to have a relatively simple assembly that typically does not result in the formation of particulates.

BRIEF SUMMARY OF THE INVENTION

Briefly stated, the present application is directed to a needle shield that is removably mountable to a syringe to protect a user from inadvertent needle pricks and generally limit contamination of a needle and a needle tip of the syringe. The needle shield includes a plug having a proximal end, a distal end and an external surface. The needle shield also includes a shell having an inner surface that defines a cavity. The plug is positioned within the cavity and a portion of the external surface of the plug is in contact with the inner surface of the shell at a contact area. The plug is non-removably bonded to the shell in at least a portion of the contact area by at least partially melting a portion of the shell and the plug in the contact area through the application of radiation energy.

In another aspect, the plug is positioned within the cavity such that a gap exists between a portion of the external surface of the plug and the inner surface of the shell. The plug is laser welded to the shell at a laser weld bond to secure the plug to the shell.

In another aspect, an annular shoulder extends from the plug near the proximal end. A shell includes an inner surface defining a cavity therein and has an open engagement end that exposes the cavity. The plug is positioned within the cavity. A securing ring is fixed to the shell through the application of radiation energy proximate the engagement end. The securing ring limits removal of the plug from the shell through interaction of the annular shoulder and the securing ring.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
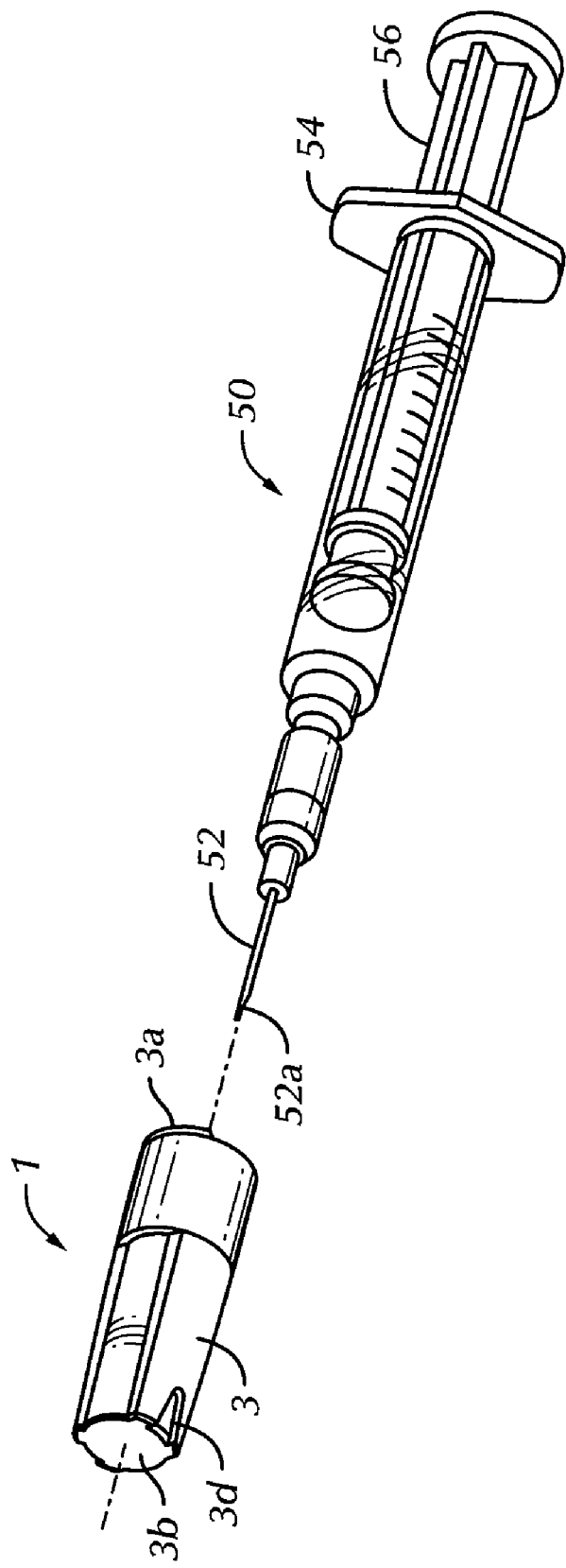
FIG. 1 is a side perspective view of a needle shield in accordance with a first preferred embodiment of the present application and a syringe that is associated with the needle shield.
Figure 2:
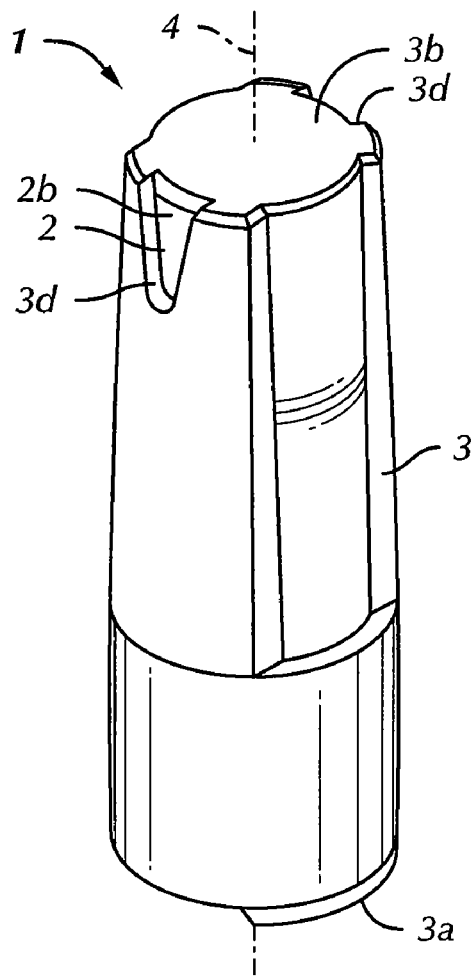
FIG. 2 is a distal end perspective view of the needle shield shown in FIG. 1.

Certain terminology is used in the following description for convenience only and is not limiting. The words, "right", "left", "lower" and "upper" designate directions in the drawings to which reference is made. The words "inwardly" and "outwardly" refer to directions toward and away from, respectively, the geometric center of the needle shields of the preferred embodiments and designated parts thereof. The terminology includes the above-listed words, derivatives thereof and words of similar import. Additionally, the word, "a" as used in the specification means, "at least one".

Figure 3:
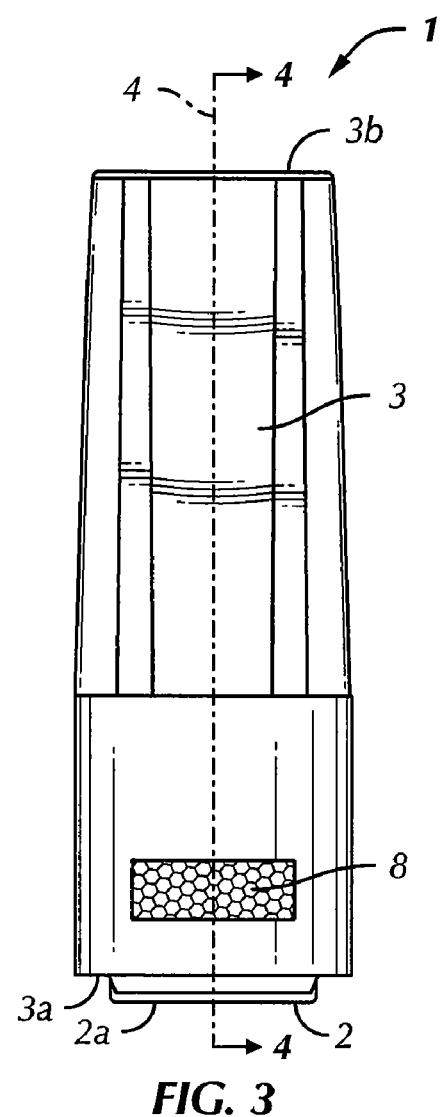
FIG. 3 is a side elevational view of the needle shield shown in FIG. 1.
Figure 4:
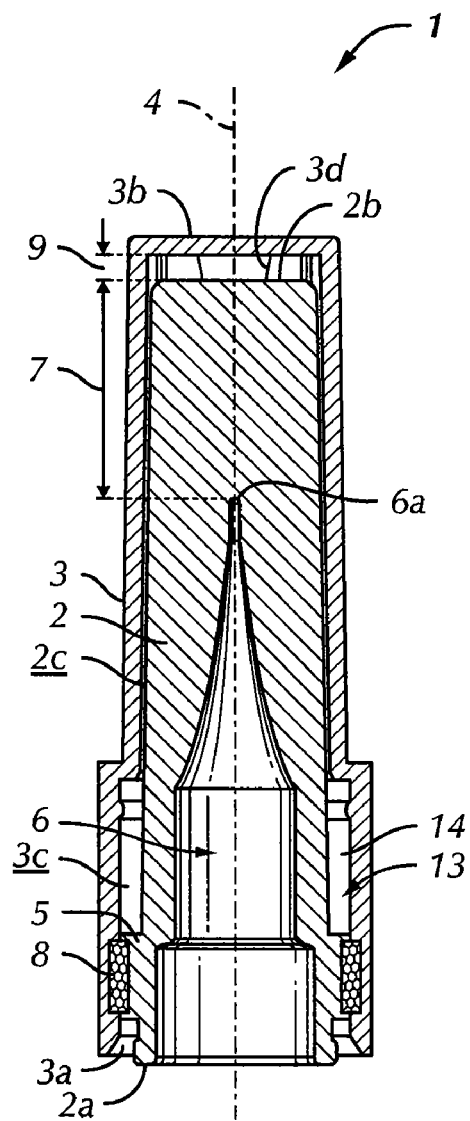
FIG. 4 is a cross-sectional view of the needle shield shown in FIG. 1, taken along line 4-4 of FIG. 3.
Figure 5:
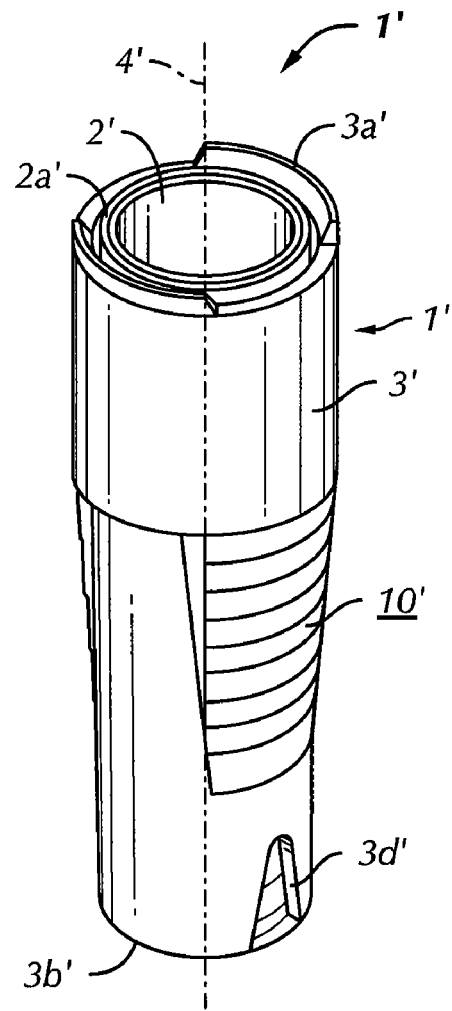
FIG. 5 is a proximal end perspective view of a needle shield in accordance with a second preferred embodiment of the present application.
Figure 6:
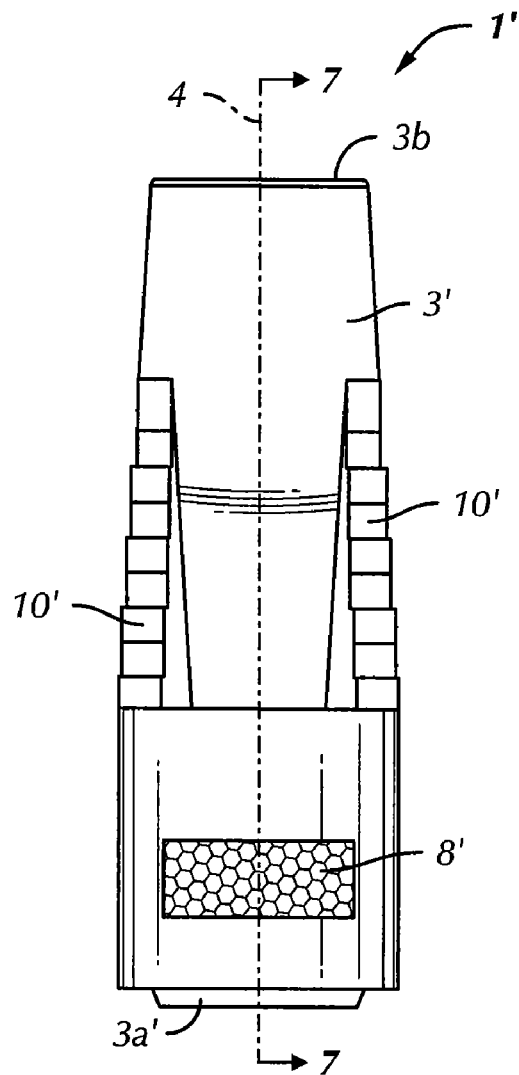
FIG. 6 is a side elevational view of the needle shield shown in FIG. 5.
Figure 7:
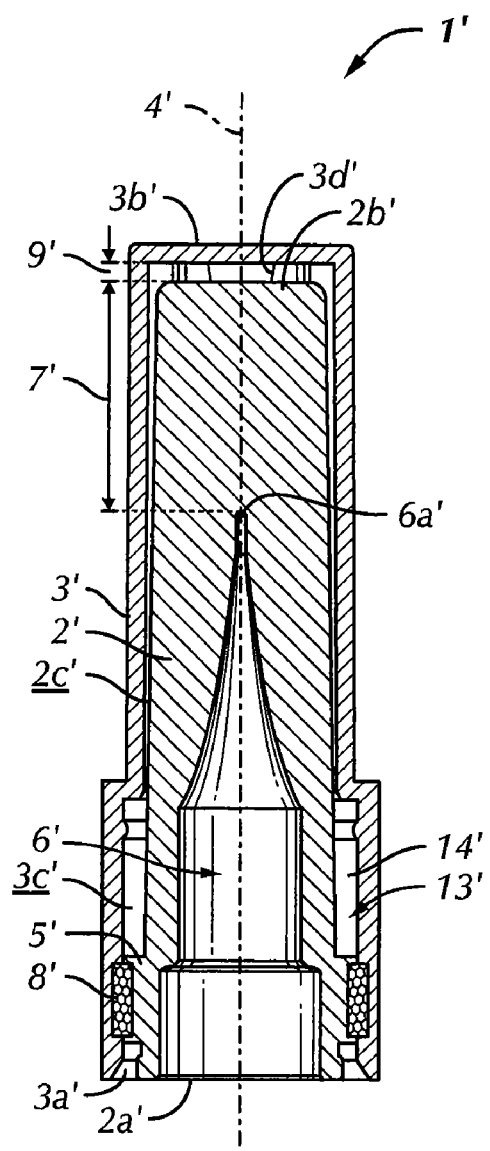
FIG. 7 is a cross-sectional view of the needle shield shown in FIG. 5 taken along line 7-7 of FIG. 6.
Figure 8:
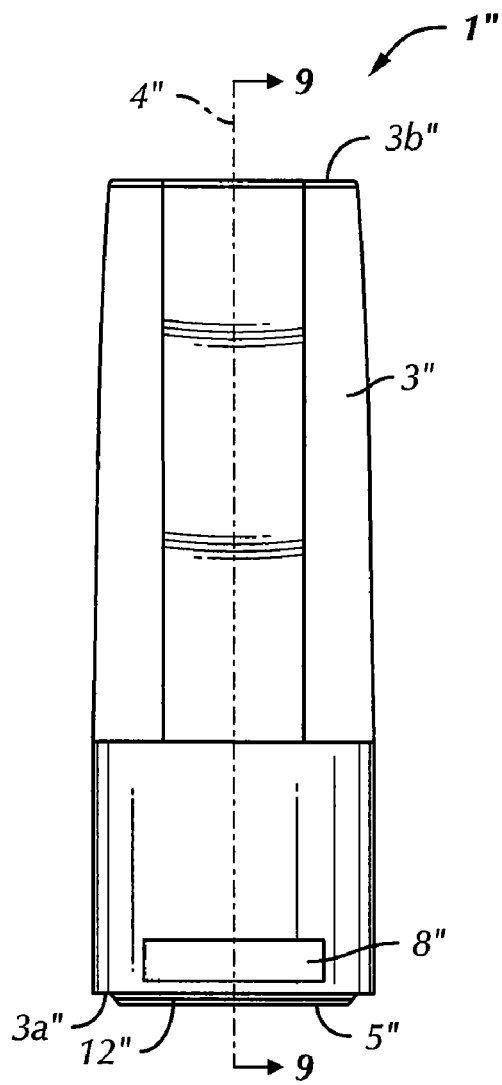
FIG. 8 is a side elevational view of a needle shield in accordance with a third preferred embodiment of the present application.
Figure 9:
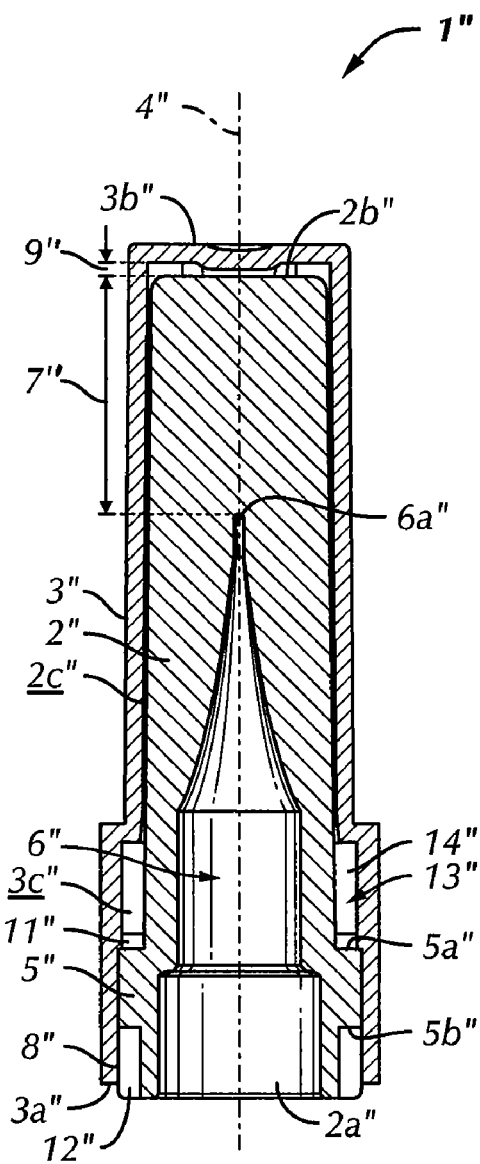
FIG. 9 is a cross-sectional view of the needle shield shown in FIG. 8, taken along line 9-9 of FIG. 8.

Referring to FIGS. 1-9, in first, second and third embodiments, the needle shield, generally designated 1, 1', 1", includes a generally rigid shell 3, 3', 3" and a relatively soft, flexible plug 2, 2', 2" mounted within the shell 3, 3', 3". The first embodiment of the needle shield 1 is shown in FIGS. 1-4, the second embodiment of the needle shield 1' is shown in FIGS. 5-7 and the third embodiment of the needle shield 1" is shown in FIGS. 8 and 9. Like elements of the first, second and third embodiments are identified by like reference numerals throughout the specification and a prime symbol (') and a double prime symbol (") are utilized to distinguish the elements of the second and third embodiments from the first embodiment, respectively. The construction and operation of the first, second and third embodiments of the needle shield 1, 1', 1" are similar and differences between the embodiments are described below, as appropriate. The needle shields 1, 1', 1" of the first, second and third embodiments are removably mountable to a syringe 50 to protect a user from inadvertent pricks from a needle 52 or needle tip 52a of the syringe 50.

Referring to FIGS. 1-4, in the first preferred embodiment, the plug 2 has a proximal end 2a and a distal end 2b. The plug 2 is preferably constructed of a thermoplastic elastomer (TPE) material and has a generally elongated, cylindrical exterior shape that is open at the proximal end 2a and closed at the distal end 2b. The plug 2 also preferably includes an external surface 2c and an annular shoulder 5 near the proximal end 2a. The plug 2 tapers slightly from a diameter at the proximal end 2a to a smaller diameter at the distal end 2b. The plug 2 is not limited to constructions utilizing the TPE material, to inclusion of the shoulder 5, to tapering from the proximal end 2a to the distal end 2b or to having a generally cylindrical shape. The plug 2 may be constructed of nearly any material that permits penetration by the syringe needle 52 and is able to withstand the normal operating conditions and perform the functions of the plug 2. However, the TPE material is preferred for the plug 2 as the material is adaptable to laser welding, as will be described in greater detail below, and is able to be penetrated by the tip 52a of the syringe needle 52. In addition, the plug 2 may have nearly any size and shape that permits interaction with the shell 3 and is adapted to perform the normal functions of the plug 2. Further, the shoulder 5 is not limited to being positioned near the proximal end 2a of the plug 2 and may be located nearly anywhere along the length of the plug 2 or may not be included on the plug 2; however, location of the shoulder 5 near the proximal end 2a is preferred such that the shoulder 5 may be secured to the shell 3 and removal forces of the syringe 50 may be reacted near the proximal end 2a, as will be described in greater detail below.

The generally rigid shell 3 is preferably constructed of a polypropylene (PP) material and includes a longitudinal axis 4. The shell 3 is not limited to constructions using the PP material and may be constructed of nearly any material that is adaptable for laser welding or other welding methods that may be adapted for welding the plug 2 to the shell 3, is able to take on the typical shape of the shell 3 and withstand the normal operating conditions and functions of the shell 3. The PP material is preferred for the shell 3 because of its adaptability to laser welding, its rigidity to protect the needle 52 and generally surround the plug 2 in a working position (not shown) and its transparency.

The shell 3 has a generally elongate, cylindrical exterior shape in the first embodiment with an engagement end 3a and a closed end 3b. The engagement end 3a is preferably open such that the plug 2 may be received into the shell 3 and the closed end 3b is preferably at least partially closed to provide a rigid barrier at the closed end 3b proximate a tip 52a of the syringe needle 52 in the working position. The shell 3 also includes an inner surface 3c that defines a cavity 13 within the shell 3. The shell 3 of the first embodiment preferably includes a pair of vent holes 3d that extend into the closed end 3b and sidewalls. The vent holes 3d preferably permit fluid flow and air flow between the shell 3 and the plug 2 for sterilization (e.g., by steam or ETO) and drying. In addition, the shell 3 preferably tapers from a cross-sectional diameter at the engagement end 3a to a smaller diameter at the closed end 3b. The shell 3 is not limited to having a generally cylindrical shape or to tapering from the engagement end 3a to the closed end 3b. For example, the shell 3 may have a generally cylindrical configuration with openings at both ends 3a, 3b or may have a generally square-shaped cross section to accept a plug 2 having a generally square-shaped cross-section.

In the first preferred embodiment, the plug 2 includes the shoulder 5 near the proximal end 2a, a plug cavity 6 having a generally funnel-shape extending from a mouth at the proximal end 2a toward the distal end 2b and a solid portion 7 extending from a cavity tip 6a of the plug cavity 6 to the distal end 2b. The plug 2 is positioned within the cavity 13 of the shell 3 such that a portion of the external surface 2c is in contact with the inner surface 3c of the shell 3 at a contact area 8. In the first preferred embodiment, the shoulder 5 is in contact with the inner surface 3c of the shell 3 to define the contact area 8 and the plug cavity 6 is exposed from the needle shield 1 at the proximal end 2a. The contact area 8 is not limited to being defined at a surface of contact between the shoulder 5 and the inner surface 3c and may be comprised of contact between nearly any portion of the external surface 2c of the plug 2 and the inner surface 3c of the shell 3. For example, the external surface 2c may be in contact with the inner surface 3c at the closed end 3b or the inner surface 3c may include several inwardly projecting ribs (not shown) that contact the external surface 2c in an assembled configuration (FIGS. 4, 7 and 9) to define the contact area 8. The needle shield 1 of the first preferred embodiment may be configured in nearly any manner wherein the inner surface 3c is in contact with a portion of the external surface 2c of the plug 2 to define the contact area 8 between the plug 2 and shell 3, such that the plug 2 may be secured to the shell 3 at the contact area 8, as will be described in greater detail below.

In the first embodiment, the shoulder 5 is preferably in contact with the inner surface of the shell 3 along a circumferentially continuous contact area 8. The plug 5 is preferably non-removably bonded to the shell 3 in at least a portion of the contact area 8 by melting a portion of the shell 3 and the plug 2 in the contact area 8 through application of radiation energy. The application of radiation energy preferably bonds the plug 2 to the shell 3 at the contact area 8 to non-removably secure the plug 2 to the shell 3. The plug 2 is preferably non-removably bonded to the shell 3 such that the plug 2 may not be removed from the shell 3 without damaging the plug 2 and/or shell 3 during the removal process. The application of radiation energy may be applied to the entire contact area 8 to bond the plug 2 to the shell 3 or may be applied at spots or only in select portions of the contact area 8 to secure the plug 2 to the shell 3. In the preferred embodiment, radiation energy is applied at the contact area through laser welding, but is not so limited and may be applied by nearly any method or mechanism that permits bonding of the plug 2 to the shell 3, such as ultrasonic welding, adhesive bonding, fastening, clamping or other heating methods that secure the plug 2 to the shell 3 in the contact area 8.

The plug 2 is not limited to inclusion of the annular shoulder 5, the plug cavity 6 or the solid portion 7 and may have nearly any shape or configuration that permits insertion of the needle tip 52a into the plug 2 and is engagable with or mountable to the shell 3. The plug 2 also preferably tapers along its length from the proximal end 2a to the distal end 2b such that the plug 2 is insertable into the engagement end 3a of the shell 3. The plug 2 is not limited to tapering from the diameter at the proximal end 2a to a smaller diameter at the distal end 2b and may be generally cylindrical or otherwise shaped, depending upon the shape of the shell 3.

In the first embodiment, the plug 2 is coaxial with the longitudinal axis 4 in the assembled configuration. The positioning of the plug 2 coaxial with the shell 3, which permits proper alignment of the needle 52 and the needle tip 52a relative to the plug 2 and shell 3 in a working position. The plug 2 is not limited to being coaxial with the shell 3 and may be arranged or located relative to the shell 3 in nearly any manner as long as the arrangement of the plug 2 relative to the shell 3 permits the welded needle shield 1 to perform its typical functions and withstand its normal operating conditions.

Referring to FIGS. 3 and 4, in the first preferred embodiment, a gap 14 is defined between a portion of the external surface 2c of the plug 2 and the inner surface 3c of the shell 3. Specifically, the extension of the annular shoulder 5 from the plug 2 near the proximal end 2a results in the contact area 8 being defined between the annular shoulder 5 and the inner surface 3c. In addition, the configuration of the plug 2 and the shell 3 results in the gap 14 being defined between the plug 2 and the shell 3 in the assembled configuration. The gap 14 permits flow of air and/or fluid between the inner surface 3c and the external surface 2c for cleaning and/or drying purposes of the plug 2 and shell 3. For example, cleaning solutions may be introduced into the gap 14 through the vent holes 3d to wash these surfaces 2c, 3c and the surfaces 2c, 3c may be subsequently dried by forcing air to circulate within the gap 14. The welded needle shield 1 is not limited to inclusion of the gap 14 and may be configured such that the external surface 2c is constantly in contact with the inner surface 3c. However, the inclusion of the air gap 14 is preferred such that air and/or fluid flow may occur in the gap 14 and such that the location of the needle 52 may be accurately tested utilizing the above-described test method of the '314 patent.

Referring to FIGS. 1-4, in the assembled configuration, a butt gap 9 is preferably defined between the distal end 2b of the plug 2 and the closed end 3b of the shell 3. Specifically, the butt gap 9 is defined between the distal end 2b of the plug 2 and the inner surface 3c at the closed end 3b of the shell 3. The butt gap 9 is comprised of a portion of the gap 14 and exposes the needle 52 to air if the needle 52 penetrates the entire plug 2, including the solid portion 7, in the working position, such that a needle tip 52a extends through the distal end 2b. The butt gap 9 permits detection of the extension of the needle 52 out of the plug 2, as will be described in greater detail below. In addition, the air gap 14 also preferably permits detection of the needle 52, if the needle 52 extends through the side of the plug 2 into the gap 14, as will also be described in greater detail below. Further, the butt gap 9 and gap 14 in conjunction with the vent holes 3d permit fluid flow and air flow around an entire periphery of the plug 2, at least outside of the contact area 8, such that the plug 2 may be cleaned using a terminal sterilization process performed on the needle shield 1 utilizing steam or other fluid sterilant. The butt gap 9, the gap 14 and the holes 3d also permit drying of the plug 2 after steam sterilization or other wet sterilization process by permitting airflow around the periphery of the plug 2.

For manufacture and assembly, the plug 2 is preferably molded using a TPE material and the shell 3 is preferably molded using a PP material. The plug 2 is inserted into the shell 3 by urging the distal end 2b through the engagement end 3a into the cavity 13. The plug 2 is positioned relative to the shell 3 such that the shoulder 5 preferably interferes uniformly, at the continuous, circumferential contact area 8 with the inner surface 3c to retain the plug 2 in position relative to the shell 3. When the plug 2 is inserted a predetermined distance or positioned at a predetermined location relative to the shell 3, a force-fit of the shoulder 5 into the shell 3 temporarily secures the plug 2 in position relative to the shell 3. The force-fit is preferred to secure the plug 2 relative to the shell 3 and to create contact between the shoulder 5 and the inner surface 3c of the shell 3 to accommodate the preferred laser welding process at the contact area 8. The shell 3 and plug 2 are then subjected to a laser welding or an alternative radiation energy operation proximate the shoulder 5, intermittently or at an entire periphery of the shoulder 5, to weld, bond or otherwise secure the plug 2 in position relative to the shell 3. The laser welding operation creates a preferably continuous laser weld bond at the contact area 8 between the inner surface 3c and the shoulder 5 to fix the plug 2 to the shell 3. The force fit of the shoulder 5 into the shell 3 and the resulting constant contact of the shoulder 5 with the shell 3 allows for a preferred consistent weld joint between the plug 2 and shell 3.

The laser weld bond at the contact area 8 is not limited to being continuous about an entire periphery of the shoulder 5 and may be comprised of spot welds at various portions of the shoulder 5 where contact is created between the shoulder 5 and the inner surface 3c of the shell 3. In addition, the laser weld bond at the contact area 8 is not limited to being located near the proximal end 2a of the plug 2, as is shown in FIGS. 3 and 4, and may be positioned nearly anywhere along the length of the plug 2 to secure the plug 2 to the shell 3. The laser welding operation is preferred for mounting the plug 2 to the shell 3 due to its relatively high speed of operation during assembly, its ability to mount the plug 2 to the shell 3 generally without creating particulates, which are common in the mechanical assembly techniques, and its adaptability for use in a clean room.

In the assembled configuration, the gap 14 is defined between the inner surface 3c of the shell 3 and the external surface 2c of the plug 2 including the butt gap 9 defined between the distal end 2b of the plug 2 and the inner surface 3c of the shell 3 proximate the closed end 3b of the shell 3. Accordingly, the gap 14, the butt gap 9 and the vent holes 3d permit flow of fluid and air around the entire exposed surface of the plug 2, outside of the contact area 8, to permit steam sterilization and drying of the plug 2 following sterilization. In addition, the plug 2 and plug cavity 6 are preferably positioned coaxial with the longitudinal axis 4 such that the cavity tip 6a and cavity 6 align with the needle tip 52a and the needle 52 in the working position.

To place the laser welded needle shield 1 in the working position relative to the syringe 50 and its associated needle 52, the needle tip 52a is inserted into the assembled, laser welded needle shield 1 through the engagement end 3a. The funnel-shape and configuration of the plug cavity 6 preferably guides the tip 52a of the needle 52 of the syringe 50 into the solid portion 7 and the plug 2 is able to flex within the shell 3 because of the gap 14 between the plug 2 and the inner surface 3c of the shell 3. The butt gap 9 also permits additional outward flexure of the plug 2 and the positioning of the contact area 8 proximate the proximal end 2a permits the plug 2 to flex toward the closed end 3b to further accommodate insertion of the tip 52a into the solid portion 7. The preferred flexing of the plug 2 relative to the needle 52 generally reduces insertion and/or removal forces. The needle 52 is inserted into the needle shield 1 until the engagement end 3a engages a portion of the syringe 50 with the needle tip 52 preferably secured in the solid portion 7. Specifically, the needle tip 52 preferably enters the solid portion 7 at the cavity tip 6a and the needle 52 is preferably coaxial with the longitudinal axis 4. Contamination of the needle 52 and needle tip 52a is typically limited or prevented and a user is generally protected from inadvertent needle pricks by the plug 2 and the rigid shell 3.

The laser welded needle shield 1 is preferably initially positioned on the syringe 50 by a syringe manufacturer or needle shield manufacturer who subsequently ships the assembled syringe 50 and needle shield 1, in the working position, to a pharmaceutical manufacturer who fills the syringe 50 with a solution. The syringe 50 is preferably filled from a plunger end 54 opposite the needle 52 where a plunger 56 is typically inserted such that the needle shield 1 is not removed from the syringe 50 during filling. The filled syringe 50 with the needle shield 1 installed thereon is subsequently shipped to an end user. The end user removes the laser welded needle shield 1 from the syringe 50 prior to injection of the solution or otherwise using the syringe 50. Accordingly, the needle shield 1 is not typically removed from the syringe 50 prior to manipulation by the user, but the assembly is not so limited and the needle shield 1 may be removed and replaced onto the syringe 50 one or more times prior to reaching the user.

The syringe 50 with the needle shield 1 mounted thereto is preferably shipped to a user with a pharmaceutical product in the syringe 50. In order to utilize the syringe 50, the needle shield 1 is manually removed from the syringe 50 to expose the needle tip 52a using finger force. The needle shield 1 is preferably manipulated by the user by applying opposing finger forces to opposing external surfaces of the shell 3 to clamp the shell 3 between the user's fingers. The preferred laser welded joint at the contact area 8 between the shoulder 5 and shell 3 typically prevents the plug 2 from breaking away from the shell 3 due to the removal forces. In addition, the gap 14, including the butt gap 9, permits flexing of the plug 2, which typically reduces the required removal forces for removing the syringe 50 from the needle shield 1. After the syringe 50 has been utilized, the syringe 50 is typically disposed of or discarded in a disposal container and the needle shield 1 may be positioned in the working position on the syringe 50 for disposal with the syringe 50.

The electronic field quality assurance test is preferably performed on the assembled needle shield 1 and syringe 50 in the working position to ensure that the needle 52 is properly positioned in the plug 2 and has not extended through the plug 2, potentially damaging the needle 52. The electronic field quality assurance test is performed by passing the assembly through an electric field which results in a spark at the portion of the needle 52 that extends into the gap 14 or the butt gap 9 between the external surface 2c of the plug 2 and the inner surface 3c of the shell 3, indicating that the needle 52 may have extended into the shell 3 and become damaged. Preferably, the needle shield 1 and the needle 52 are discarded if the needle 52 extends into the gap 14, including the butt gap 9, which is preferably detected utilizing the electronic field quality assurance test. The assembled needle shield 1 and syringe 50 are also preferably visually inspected to eliminate defects that are visually apparent to an inspector, where a decision may be made whether to dispose of the needle shield 1 and/or syringe 50.

Referring to FIGS. 5-7, in the second preferred embodiment, the shell 3' preferably includes a ribbed, grasping or gripping surface 10' on its external surface that provides a grasping area for a user such that the needle shield 1' is relatively easy for the end user to grasp and manipulate. In the second embodiment, the gripping surface 10' is comprised of a series of ribs on opposed, external sides of the shell 3'. The gripping surfaces 10' are conveniently located for the user to grasp with a thumb and finger for removing the needle shield 1' from the syringe 50. The needle shield 1' is not limited to inclusion of the ribbed gripping surfaces 10' and may function appropriately without the gripping surfaces 10 or may include alternate gripping surfaces 10' that provide a grasping surface for the user or for syringe and/or pharmaceutical manufacturers, as will be apparent to one having ordinary skill in the art based upon the present disclosure.

Referring to FIGS. 8 and 9, in the third preferred embodiment, the plug 2" is constructed of a relatively soft polymeric material, such as a rubber material that is generally not suitable for laser welding to the shell 3". Accordingly, once the plug 2" is inserted into the shell 3", the laser welding operation is typically unable to secure the plug 2" to the shell 3". Therefore, the shell 3" of the third preferred embodiment includes a positioning rib 11" extending radially inwardly from the inner surface 3c" and a securing ring 12" that is preferably laser welded to the shell 3" proximate the engagement end 3a" at a laser weld bond in the contact area 8". The annular shoulder 5" includes a first edge 5a" and a second edge 5b", wherein the first edge 5a" is in contact with the positioning rib 11 and the second edge 5b" is in contact with the securing ring 12" in the assembled configuration. Accordingly, in the third preferred embodiment, the annular shoulder 5" of the plug 2" is secured between the laser welded securing ring 12" and the positioning rib 11" within the cavity 13" of the shell 3".

The securing ring 12" is preferably constructed of a PP material or other material that is weldable to the shell 3" and has a generally ring-shape. The securing ring 12" is not limited to constructions utilizing the PP material or to having a continuous, ring-shape. The securing ring 12" may be constructed of nearly any material that is adapted to laser welding to the shell 3" at the contact area 8" or to being secured to the shell by nearly any method or mechanism including adhesive bonding, heat or ultrasonic melting, fastening or other securing processes. The securing ring 12" may be constructed of several arc-shaped wedges that are individually laser welded to the shell 3" at the weld bond in the contact area 8" to secure the shoulder 5" of the plug 2" between the positioning rib 11" and the securing ring 12". In addition, the positioning rib 11" is preferably continuous and integrally molded into the shell 3", but is not so limited. The positioning rib 11" may be comprised of integrally molded, arc-shaped wedges (not shown) that extend from the inner surface 3c" or may be comprised of a separate ring-shaped or several arc-shaped segments that are laser welded or otherwise bonded to the inner surface 3c" at a position to locate the plug 2" at a preferred position within the shell 3".

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

We claim:

1. A needle shield that is removably mountable to a syringe to protect a user from inadvertent needle pricks and generally limit contamination of a needle and needle tip of the syringe, the needle shield comprising:
    a plug including a proximal end, a distal end and an external surface; and
    a shell including an inner surface defining a cavity therein, the plug being positioned within the cavity, a portion of the external surface of the plug being in contact with the inner surface of the shell at a contact area, a laser weld bond non-removably securing the plug to the shell, the plug being non-removably bonded to the shell in at least a portion of the contact area by at least partially melting a portion of the shell and the plug in the contact area through application of radiation energy.

2. The needle shield of claim 1 further comprising:
    a gap defined between a portion of the external surface of the plug and the inner surface of the shell.

3. The needle shield of claim 2 further comprising:
    vent holes located proximate a closed end of the shell that permit circulation of fluid in the gap.

4. The needle shield of claim 1 further comprising:
    a gripping surface located on an exposed surface of the shell, the gripping surface providing a grasping surface for manipulation of the needle shield by a user.

5. The needle shield of claim 1 further comprising:
    an annular shoulder located on the external surface of the plug near the proximal end of the plug, the contact area being defined by contact between the annular shoulder and the inner surface of the shell.

6. The needle shield of claim 5 wherein the contact area is circumferentially continuous on the annular shoulder.

7. The needle shield of claim 1 wherein the shell includes an engagement end and a closed end, the shell having a generally cylindrical-shape and a larger diameter at the engagement end compared to the closed end.

8. The needle shield of claim 1 wherein the plug includes a plug cavity having an open mouth at the proximal end and a cavity tip opposite the mouth, the plug cavity having a funnel-shape extending from the cavity tip toward the mouth.

9. The needle shield of claim 8 wherein the plug includes a solid portion between the cavity tip and the distal end.

10. The needle shield of claim 1 wherein the plug is constructed of a thermoplastic elastomer material and the shell is constructed of a relatively rigid thermoplastic material.

11. A needle shield removably mountable to a syringe to protect a user from inadvertent needle pricks and generally limit contamination of a needle and needle tip of the syringe, the needle shield comprising:
    a plug including a proximal end, a distal end and an external surface; and
    a shell including an inner surface defining a cavity therein, the plug being positioned within the cavity such that a gap exists between a portion of the external surface of the plug and the inner surface of the shell, a laser weld bond securing the plug to the shell.

12. The needle shield of claim 11 further comprising:
    an annular shoulder extending from the external surface of the plug near the proximal end, the annular shoulder being in contact with the inner surface of the shell at a contact area, the laser weld bond being located at the contact area.

13. The needle shield of claim 11 further comprising:
    vent holes located in the shell; and
    a gap defined by the inner surface of the shell and the external surface of the plug, the vent holes being in communication with the gap to permit circulation of fluid within the gap.

14. A needle shield removably mountable to a syringe to protect a user from inadvertent needle pricks and generally limit contamination of a needle and needle tip of the syringe, the needle shield comprising:
    a plug including a proximal end, a distal end and an external surface, an annular shoulder extending from the external surface of the plug near the proximal end;
    a shell including an inner surface defining a cavity therein and having an open engagement end that exposes the cavity, the plug being positioned within the cavity; and
    a securing ring fixed to the shell through the application of radiation energy proximate the engagement end, a laser weld bond fixing the securing ring to the shell and the securing ring limiting removal of the plug from the shell through interaction of the annular shoulder and the securing ring.

15. The needle shield of claim 14 further comprising:

a positioning rib extending inwardly from the inner surface toward a longitudinal axis of the needle shield, the annular shoulder having a first edge and a second edge, the first edge being in contact with the positioning rib and the second edge being in contact with the securing ring.

16. The needle shield of claim 14 wherein the plug is constructed of a soft polymeric material, the shell and the securing ring constructed of a relatively rigid plastic material.

17. The needle shield of claim 16 wherein the soft polymeric material is a rubber material.

* * * * *